United States Patent [19]
Murphy

[11] Patent Number: 6,121,497
[45] Date of Patent: Sep. 19, 2000

[54] PROCESS OF RECOVERING METHYL ETHYL KETONE FROM AN AQUEOUS MIXTURE OF METHYL ETHYL KETONE AND ETHANOL

[75] Inventor: Carl David Murphy, Corpus Christi, Tex.

[73] Assignee: Celanese International Corporation, Dallas, Tex.

[21] Appl. No.: 09/173,620

[22] Filed: Oct. 16, 1998

[51] Int. Cl.[7] .................................................. C07C 45/78
[52] U.S. Cl. ........................ 568/410; 568/388; 568/913
[58] Field of Search .................................... 568/410, 913, 568/388; 203/57, 60, 61, 62, 63, 70

[56] References Cited

U.S. PATENT DOCUMENTS

| | | | |
|---|---|---|---|
| 2,528,761 | 11/1950 | Lake et al. | 202/42 |
| 3,404,186 | 10/1968 | Bailey et al. | 260/593 |
| 5,453,166 | 9/1995 | Berg | 203/57 |

*Primary Examiner*—Johann Richter
*Assistant Examiner*—Sreeni Padmanabhan
*Attorney, Agent, or Firm*—M. Susan Spiering

[57] ABSTRACT

A process for the recovery of methyl ethyl ketone (MEK) from an aqueous mixture of MEK and ethanol comprising extracting the MEK from the mixture using an extractive solvent selected from the group consisting of isopentane, the o-, m-, m-isomers of xylene, and mixed xylenes. Preferably the extractive solvent is separated from the MFK in the extract by fractional distillation and recycled to the extraction step.

7 Claims, 2 Drawing Sheets

6,121,497

PROCESS OF RECOVERING METHYL ETHYL KETONE FROM AN AQUEOUS MIXTURE OF METHYL ETHYL KETONE AND ETHANOL

BACKGROUND OF THE INVENTION

Field of the Invention

This invention relates to an improved process for the recovery of methyl ethyl ketone (MEK) from an aqueous mixture comprising MEK and ethanol (EtOH).

Description of the Related Art Including Information Disclosed Under 17 CFR 1.97 and 1.98 Various chemical processes are known which include the step of recovering ethanol (EtOH) and methyl ethyl ketone (MEK) in satisfactory yields from an aqueous mixture of the two compounds. One method of recovery which has been used is solvent extraction using a solvent which selectively extracts MEK from the aqueous mixture. Most of the MEK is removed from the solvent by fractional distillation and the solvent is recycled to the solvent extraction unit. However, a disadvantage of this method often encountered is that either the recycled solvent contains a relatively large amount of MEK resulting in a lower than desired recovery of MEK product obtained from the solvent extraction, or that a greater than desired amount of energy is expended in removing MEK from the recycled solvent in order to obtain a satisfactory yield of MEK. Thus, any improvement in the process resulting in the elimination or reduction of these disadvantages would be very valuable.

U.S. Pat. No. 2,528,761, issued Nov. 7, 1950 to Lake, et. al., discloses a process of separating an alcohol from a ketone by azeotropic distillation using an aromatic hydrocarbon or an alkyl derivative of an aromatic hydrocarbon as an azeotrope former. For example, ethyl alcohol may be separated from MEK using benzene as the azeotrope former, or a higher boiling alcohol and ketone may be separated using a xylene isomer or mixture of such isomers as the azeotrope former.

U.S. Pat. No. 3,404,186 issued Oct. 1, 1968 to Bailey, et. al., discloses a process for the recovery of EtOH and MEK from a MEK-ethyl acetate mixture comprising hydrolyzing at least a portion of the ethyl acetate, distilling the resulting hydrolysis product comprising MEK, EtOH, acetic acid (HOAc) water and unhydrolyzed ethyl acetate to obtain a residue comprising HOAc and water and a distillate comprising unhydrolyzed ethyl acetate, MEK and EtOH, subjecting the latter distillate to a second distillation to obtain a distillate comprising low-boiling impurities, unhydrolyzed ethyl acetate and a ternary azeotrope of MEK, water and EtOH, and a residue comprising MEK and EtOH, mixing the latter residue with water, and extracting MEK from the resulting aqueous mixture using a hydrocarbon such as n-pentane as extractant.

U.S. Pat. No. 5,453,166, issued Sept. 26, 1995 to Berg, teaches a method for 5 the separation of ethanol from 2-butanone (MEK) by extractive distillation using an extractive agent which may be any of the three xylene isomers.

BRIEF SUMMARY OF THE INVENTION

In accordance with this invention, MEK is recovered from an aqueous mixture comprising MEK and EtOH by solvent extraction using as extractive solvent a member selected from the group consisting of isopentane, o-, m,- and p-xylene, and mixed xylenes. Preferably, the extractive solvent is separated from the MEK in the extract by fractional distillation and recycled to the extraction step.

The aqueous mixture comprising MEK and EtOH from which MEK is extracted by means of the inventive method may be obtained, for example, in the course of the purification of the product of the liquid phase oxidation of a $C-C_6$ aliphatic hydrocarbon such as n-butane with molecular oxygen, specifically the aftertreatment of a distillate fraction of the product comprising MEK and ethyl acetate.

DETAILED DESCRIPTION OF THE INVENTION

The raw product from the liquid phase oxidation with molecular oxygen of $C_3-C_6$ hydrocarbons, such as n-butane, may be fractionally distilled to obtain several fractions including one containing substantial amounts of MEK and ethyl acetate. Streams containing major proportions respectively of MEK and EtOH may be recovered from the MEK-ethyl acetate fraction by at least partially hydrolyzing the ethyl acetate to ethanol and acetic acid, using an acid catalyst such as an acidic ion-exchange resin, e.g., sulfonated polystyrene, subjecting the hydrolysis products to a distillation step from which the residue comprises acetic acid and most of the water and the distillate comprises unhydrolyzed ethyl acetate, MEK, and EtOH. Such distillate may be subjected to a second distillation in which low boiling impurities are removed as a distillate comprising a ternary azeotrope of MEK, water and EtOH, while the residue containing MEK and EtOH is mixed with water to obtain an aqueous mixture from which MEK may be extracted using an extractive solvent which has a greater degree of affinity for MEK than for EtOH. A stream containing a major proportion of MEK may be separated from the extract by distillation and a stream containing a major proportion of EtOH may be obtained from the raffinate using conventional means, primarily distillation, with the extractive solvent after removal of the bulk of the MEK being recycled to the solvent extraction step. A form of this process is described in previously cited U.S. Pat. No. 3,404,186, the entire disclosure of which is hereby incorporated herein by reference.

Figure 1:
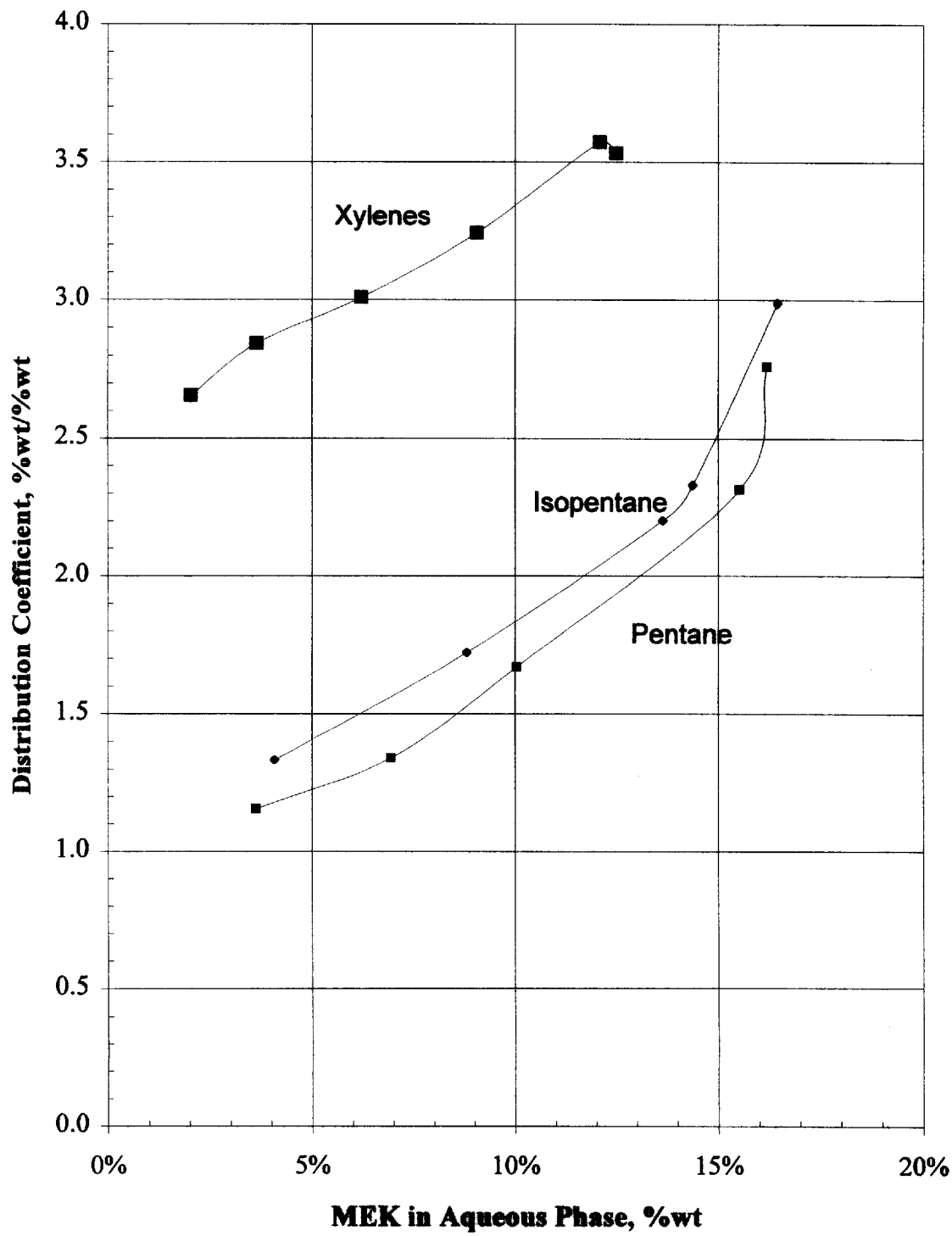
FIG. 1 shows curves of MEK Distribution Coefficients plotted against content of MEK in the aqueous phase (raffinate) determined for isopentane, mixed xylenes and pentane, i.e., n-pentane, utilized as extractive solvent in the solvent extractions.

As stated previously, this invention contemplates the separation of MEK from an aqueous mixture of MEK and EtOH, e.g., obtained in the course of carrying out the overall process described hereinbefore, by solvent extraction using as the extractive solvent a member selected from the group consisting of isopentane, the o-, m-, and p-isomers of xylene and mixed xylenes. The use of any of these solvents yields superior results both in the extraction of MEK from the aqueous mixture feed to the solvent extraction step and in the separation by distillation of the solvent from most of the MEK in the extract. Thus, as shown in FIG. 1, curves obtained by plotting the distribution coefficient of MEK against the wt. % of MEK in the aqueous phase, i.e., the raffinate, when MEK is extracted from an aqueous mixture of MEK and EtOH using isopentane, mixed xylenes and n-pentane as solvent, indicate that the distribution coefficients obtained with isopentane and mixed xylenes are higher than those obtained with n-pentane. The distribution coefficients indicated in these curves are defined as the ratio of the wt. % of MEK in the extract to the wt. % of MEK in the raffinate at equilibrium, and the values were determined by standard means of aqueous mixtures wherein the percentage of MEK was varied to obtain the desired wt. % of MEK in the raffinate. The experiment was done by blending various amounts of MEK with a stock solution of 23% EtOH in water and extracting those mixtures with pure solvent. The curves indicate that isopentane and xylenes are unexpectedly more effective in extracting MEK from aqueous mixtures of MEK and EtOH than is a conventionally used solvent, such as n-pentane.

Figure 2:
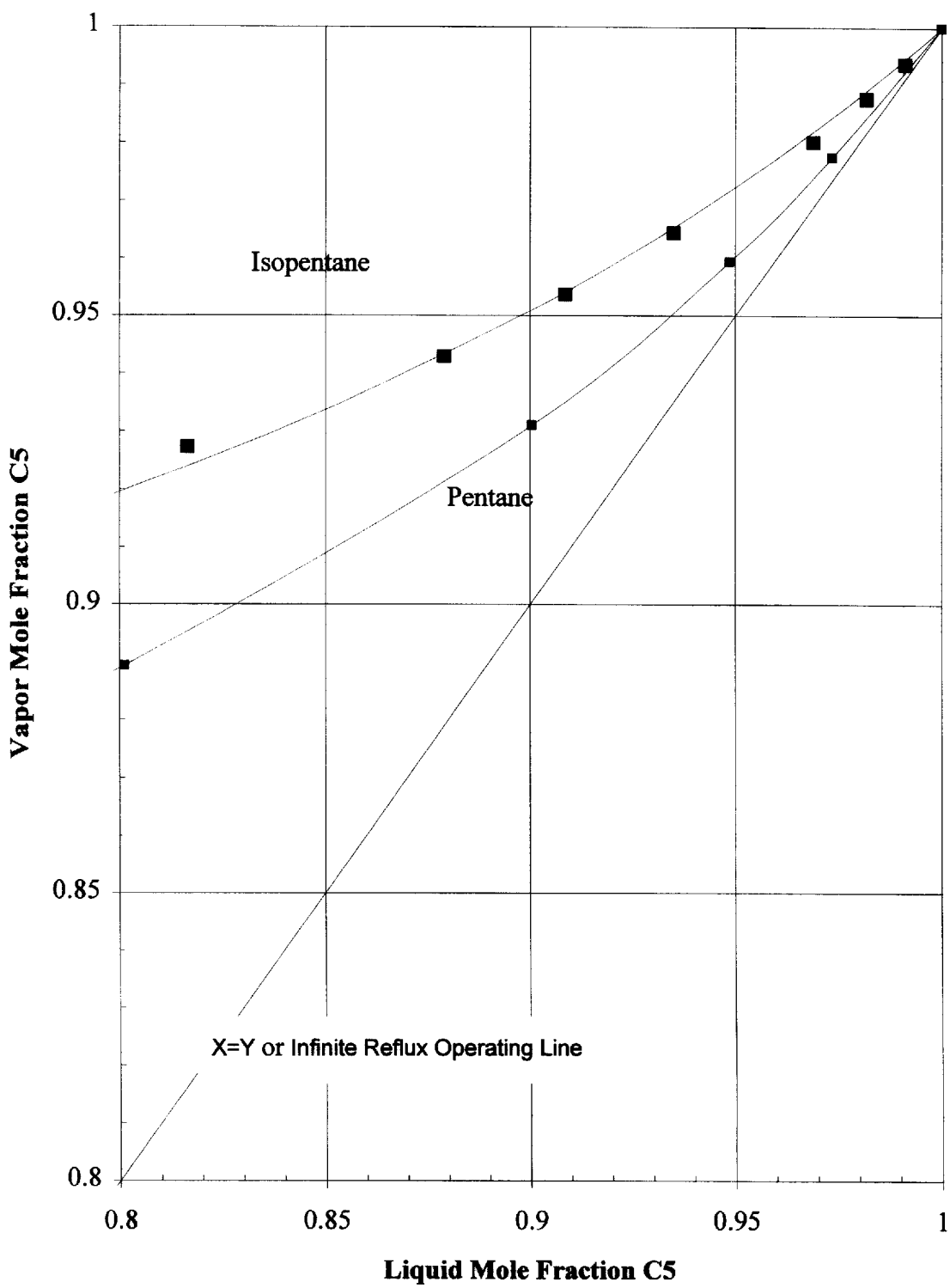
FIG. 2 shows Vapor Liquid Equilibrium (VLE) curves for isopentane and n-pentane. each mixed with MEK as applied to separation of MEK from the $C_5$ solvent in the extract of the solvent extraction by distillation.

The curves shown in FIG. 2 are vapor liquid equilibrium (VLE) curves for binary mixtures of MEK with extractive $C_5$ solvents isopentane and n-pentane respectively, and were obtained by plotting the mole fraction of the $C_5$ solvent in the MEK-solvent liquid mixture against the mole fraction of such solvent obtained by vaporizing such liquid mixture in one stage at equilibrium. The significance of these VLE curves is that the closeness of the curve to the x=y or infinite reflux operating line, termed the "pinch", indicates the degree of difficulty of separating the two components by distillation, with the closer the curve, i.e., the more severe the pinch, the more difficult the separation. As shown in FIG. 2, the VLE curve for isopentane indicates a less severe pinch than that for n-pentane, indicating that when isopentane solvent is the extractive solvent utilized in the solvent extraction of MEK, the separation of MEK from the extract is unexpectedly more easily accomplished than when n-pentane is the solvent. Since the VLE curve for MEK and p-xylene is even better, i.e., has an even less severe pinch than that for isopentane, it can be concluded that the separation of MEK from a xylene solvent is even more easily accomplished than when isopentane is the solvent.

The advantages of the solvents of this invention over a known solvent, n-pentane, as described hereinbefore, are obtained with no sacrifice of selectively of MEK over EtOH, which tends to be approximately equivalent for all the solvents discussed at high MEK concentrations, i.e., those which are most important in the extraction. Selectivity in this context is defined as the ratio of the distribution coefficient of MEK to that of EtOH.

The aqueous mixture of MEK and EtOH intended to be fed to the solvent extraction of this invention, which may be obtained as part of the larger purification process described previously, may contain, for example, from about 15 to about 45 wt. % of MEK, from about 10 to about 25 wt. % of EtOH, from about 40 to about 60 wt. % of water and from about 1 to about 5 wt. % other organic compounds, such as ethyl acetate. The weight ratio of solvent to feed may be in the range, for example, of about 0.3 to about 2 and the extraction may be carried out at a temperature of, for example, from about 25 to about 50° C., and any pressure high enough to assure that the volatile solvent remains a liquid. The extraction is preferably carried out countercurrently in a staged solvent extractor equipped with, for example, with from about 3 to about 30 trays, with the extractive solvent being injected at the bottom and the feed entering the top of the tower.

The extract comprising most of the MEK in the feed mixture may contain, for example, from about 10 to about 20 wt. % of MEK, from about 80 to about 90 wt. % of solvent and a small amount of other materials, such as ethyl acetate, while the raffinate comprising most of the ethanol and water in the feed mixture may contain, for example, from about 10 to about 30 wt. % of ethanol, from about 65 to about 85 wt. % of water, from about I to about 10 wt. % of MEK and a minor amount of other organic compounds.

The extract from the solvent extractor is generally distilled to recover solvent for recycle to the extractor. Such distillation is preferably carried out in a fractional distillation column containing, for example, from about 15 to 50 trays, wherein the temperature at the top of the column is, for example, from about 50 to about 70° C. and the temperature at the bottom is, for example, from about 100 to about 130° C., with the extract being fed to an intermediate tray. The distillate withdrawn from the top of the distillation column comprises a major proportion, i.e., over 50 wt. % of extractive solvent, and may contain, for example, from about 1 to about 10 wt. % of MEK, and is recycled to the bottom of the solvent extractor, while the residue taken from the bottom of the distillation column is crude MEK containing a major proportion, i.e., over 50 wt. % of MEK, part or all of which may be purified by conventional means for various uses, and any remainder recycled, for example, to a liquid phase hydrocarbon oxidation process, as described previously, for further oxidation to carboxylic acids.

The raffinate from the solvent extractor may be purified by conventional means to obtain products containing varying amounts of ethanol and water for different applications.

In a combined operation of solvent extraction in a staged extractor and separation of solvent from the extract in a fractional distillation column as described hereinbefore, use of isopentane or a xylene or mixed xylenes as extractive solvent results in the separation of crude MEK from an aqueous mixture of MEK and EtOH with less consumption of energy and/or lower capital expenditure as compared with the use of a conventional solvent such as n-pentane to separate an equivalent amount of crude MEK from the same mixture. The reason for this is that both the higher distribution coefficients shown in FIG. 1 and the less severe pinch illustrated in FIG. 2 of a solvent under the invention result in a tendency, under similar conditions of equipment size and energy consumption, for the percentage of MEK in the extract from the extractor to be higher and in the recycled distillate from the distillation to be lower when an extractive solvent under the invention is utilized than when a conventional solvent such as n-pentane is employed. Further, a higher percentage of MEK in the solvent distillate recycled to the extractor results in the presence of a greater amount of MEK in the raffinate from the extractor which cannot be directly recovered as product. Moreover, in view of the higher heat of vaporization of MEK as compared with those of the solvents of this invention or of conventional solvents such as n-pentane, a higher reflux ratio can be used in the distillation column at the same level of energy supplied to the reboiler when an extractive solvent under the invention is used such that a relatively low percentage of MEK is in the distillate recycled to the extractor than when a conventional solvent such as n-pentane is the extractive solvent resulting in a higher proportion of MEK in the distillate. This contributes further to a minimization of the energy required to circulate MEK between the extractor and the distillation column, and the loss of MEK from the product when an extractive solvent under the invention is used as compared with the use of a conventional solvent such as n-pentane.

A corollary of the foregoing discussion is that if it is desired to operate the process with a conventional extractive solvent such as n-pentane and obtain the same crude MEK production from an identical aqueous feed mixture of MEK and EtOH as when an extractive solvent under the invention is used, it would be necessary to use larger equipment, e.g., an extractor and/or distillation column having a larger number of trays, and/or a larger amount of reboiler energy in the distillation column to obtain a higher reflux ratio.

The following comparative examples further illustrate the invention.

EXAMPLE 1 AND COMPARATIVE EXAMPLE A

These examples describe the separation of MEK from an identical aqueous feed mixture comprising MEK and EtOH, by means of a process as described hereinbefore with the system in each example utilizing an identical solvent extraction equipped with 20 trays to extract MEK from the feed mixture and an identical distillation column equipped with 36 trays to separate MEK from the extract. The system in both examples is designed to produce about 13,000 lb/hr of MEK and the conditions of operation are kept as close as possible in the two examples except that the extractive solvent is isopentane in Example 1 and n-pentane in Comparative Example A. Thus, because of the different properties of the two solvents, certain conditions of the process in each example are necessarily different, such as the percentage of MEK in the various streams.

In both examples, an aqueous mixture at a temperature of about 32° C. and containing about 59 wt. % of MEK, about 9 wt. % of ethanol, about 22 wt. % of water and about 9 wt. % of other organic compounds, was fed near the top of the extractor, and the extractive solvent, viz. isopentane in Example 1 and n-pentane in Comparative Example A, each containing a minor amount of MEK which is the distillate from the distillation column, is recycled to the bottom of the extractor. The extraction is carried out at a temperature of about 31° C. and a pressure of about 43 psia. The extract withdrawn from the top of the extractor which is composed primarily of the extractive solvent with most of the remainder being the extracted MEK, is fed to tray 21 of the distillation column, while the raffinate from the extractor containing about 28 wt. % of ethanol, about 64 wt. % of water, and differing amounts of MEK and other organic compounds in each example, may be treated by conventional methods to obtain various ethanol-containing products.

As stated, the distillate from the distillation column composed primarily of extractive solvent containing a minor amount of MEK differing in the two examples is fed near the top of the extractor. The residue from the distillation column is the main product of the process, i.e., crude MEK composed primarily of MEK with minor amounts of other organic compounds. It may be purified by conventional means to obtain various MEK-containing products suitable for particular applications.

Table 1 shows various conditions of the solvent extraction of the two examples not given in the foregoing discussion.

TABLE I

| EXAMPLE | 1 | A |
|---|---|---|
| Solvent/feed ratio, lb/lb | 1.2 | 1.2 |
| MEK in solvent, wt. % | 3.4 | 7.8 |
| MEK in raffinate, wt. % | 2.0 | 4.6 |
| MEK in raffinate, lb/hr | 690 | 1,580 |

As discussed previously, the lower percentage of MEK in the isopentane solvent and raffinate of Example 1 than in the n-pentane solvent and raffinate of Comparative Example A is due to a combination of unexpectedly higher distribution coefficient of isopentane than of n-pentane with respect to MEK in the raffinate as shown in FIG. 1 and the less severe pinch of the VLE curve of isopentane than that of n-pentane with respect to mixtures of each solvent with MEK as shown in FIG. 2, which results in a lower percentage of MEK in the distillate of Example 1 recycled as solvent to the reactor than in the distillate of Comparative Example A.

Moreover, the larger percentage of MEK in the raffinate of Comparative Example A represents a greater loss of MEK product due to the extraction with an n-pentane solvent than occurs with an isopentane solvent.

Table II shows conditions of the distillation of the extract in the two examples which were not given in the foregoing discussion.

TABLE II

| EXAMPLE | 1 | A |
|---|---|---|
| MEK in feed, wt. % | 26 | 26 |
| MEK in distillate, wt. % | 3.4 | 7.8 |
| Reboiler energy Btu/lb distillate | 250 | 240 |
| Reflux ratio | 0.33 | 0.24 |
| Tower top pressure, psia | 40 | 34 |
| Tower top temperature, C | 60 | 63 |

When, as indicated in Table II, the percentage of MEK in the feed to the distillation column, which is the extract from the solvent extractor, is the same for the isopentane and n-pentane employed as the extractive solvents in Example 1 and Comparative Example A respectively, then the less severe pinch of the VLE curve for isopentane than that for n-pentane as shown in FIG. 1 results in the distillate having a lower percentage of MEK at the same reflux ratio when isopentane is the extractive solvent being treated to separate MEK than when n-pentane is the solvent. Moreover, because of the substantially higher heat of vaporization of MEK than that of isopentane and n-pentane, the distillation of isopentane resulting in a lower percentage of MEK in the distillate than the distillation of n-pentane, can be accomplished at the same reflux ratio with a significantly lower reboiler energy than is consumed with n-pentane.

However, because the reboiler energy consumed is a very important economic factor in distillation, the reflux ratio employed in Example I is adjusted to be somewhat higher than that of Comparative Example A such that the reboiler energy consumption is approximately equal in both examples, as shown in Table II. This has the effect of improving the separation of MEK from the isopentane solvent of Example 1, thus further reducing the percentage of MEK in the distillate which is recycled to the extractor as solvent.

The employment of a single xylene isomer or a mixture of more than one of such isomers as the extractive solvent in the process of this invention also shows improved performance over the use of n-pentane, of the type brought out in the discussion hereinbefore of the use of isopentane as solvent.

I claim:

1. A process for the separation of methyl ethyl ketone (MEK) from an aqueous mixture containing MEK and ethanol (EtOH) comprising subjecting the mixture to solvent extraction using as extractive solvent a member selected from the group consisting of isopentane, the o-, m,- and p-isomers of xylene and mixed xylenes.

2. The process of claim 1 herein said solvent is isopentane.

3. The process of claim 1 wherein said solvent is a xylene isomer or a mixture of xylene isomers.

4. The process of claim 1 wherein the extract from said extraction comprising said solvent and MEK is subjected to fractional distillation to obtain a distillate containing a over 50 wt. %. proportion of said solvent which is recycled to said solvent extraction, and a crude MEK residue.

5. The process of claim 1 where said aqueous mixture is obtained from a mixture of MEK and ethyl acetate by at least partially hydrolyzing the ethyl acetate in the mixture to form a hydrolysis product comprising MEK, EtOH, acetic acid (HOAc), water and unhydrolyzed ethyl acetate, subjecting said hydrolysis product to a distillation step from which the residue comprises HOAc and most of the water and the distillate comprises unhydrolyzed ethyl acetate, MEK and EtOH, subjecting the latter distillate to a second distillation in which the distillate comprises low boiling impurities, unhydrolyzed ethyl acetate, and a ternary azeotrope of MEK, water and EtOH, and the residue comprises MEK and EtOH, and adding water to the latter residue.

6. The process of claim 5 wherein said mixture of MEK and ethyl acetate is obtained as a fraction from the distillation of the products resulting from the liquid phase oxidation with molecular oxygen of a $C_3$–$C_6$ aliphatic hydrocarbon.

7. The process of claim 6 wherein said hydrocarbon is n-butane.

\* \* \* \* \*